United States Patent
Howes et al.

(10) Patent No.: US 9,551,600 B2
(45) Date of Patent: Jan. 24, 2017

(54) SYSTEM AND METHOD FOR CREATING A FLOW CYTOMETER NETWORK

(75) Inventors: Grant C. Howes, Ann Arbor, MI (US); Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 1052 days.

(21) Appl. No.: 13/697,739

(22) PCT Filed: Jun. 14, 2011

(86) PCT No.: PCT/US2011/040365
§ 371 (c)(1),
(2), (4) Date: Dec. 12, 2012

(87) PCT Pub. No.: WO2011/159708
PCT Pub. Date: Dec. 22, 2011

(65) Prior Publication Data
US 2013/0080082 A1 Mar. 28, 2013

Related U.S. Application Data

(60) Provisional application No. 61/354,577, filed on Jun. 14, 2010.

(51) Int. Cl.
*G01F 1/00* (2006.01)
*G01F 25/00* (2006.01)
(Continued)

(52) U.S. Cl.
CPC ............ *G01F 1/00* (2013.01); *G01F 25/0007* (2013.01); *G01N 15/14* (2013.01);
(Continued)

(58) Field of Classification Search
CPC ........ G01F 1/00; G01F 25/0007; G06F 17/00; G06F 19/28; G01N 15/14; G01N 35/00871
See application file for complete search history.

(56) References Cited

U.S. PATENT DOCUMENTS 3,347,273 A 10/1967 Russell
3,601,128 A 8/1971 Hakim
(Continued)

FOREIGN PATENT DOCUMENTS

EP 466490 A 1/1992
EP 0602416 A 6/1994
(Continued)

OTHER PUBLICATIONS

Light, 2006, 2 pages. Collins Dictionary of Astronomy. Long, United Kingdom. Retrieved online on Jul. 26, 2015 from <<http://www.credoreference.com>>.
(Continued)

*Primary Examiner* — Alexander Satanovsky
*Assistant Examiner* — John Kuan
(74) *Attorney, Agent, or Firm* — Jeffrey Schox; Ivan Wong

(57) ABSTRACT

A system for creating a flow cytometer network includes: a flow cytometer with an interrogation zone and a fixed gain detection system that collects sample data from the interrogation zone; a flow cytometer data center that stores and manages sample-related data from the flow cytometer; and a network communication module that communicates sample-related data between the flow cytometer and the data center. The system may include a second flow cytometer and a second network communication module, where the first and second flow cytometers are calibrated to have substantially identical fixed gain settings. A method for creating a flow cytometer network includes: calibrating first and second flow cytometers with a calibration solution; collecting
(Continued)

sample data with a fixed gain detection system; uploading data to a flow cytometer data center; retrieving data from the data center; and performing data analysis on the retrieved data.

25 Claims, 3 Drawing Sheets

(51) Int. Cl.
- *G01F 17/00* (2006.01)
- *G01N 15/14* (2006.01)
- *G01N 35/00* (2006.01)
- *G06F 19/28* (2011.01)
- *G06F 17/00* (2006.01)

(52) U.S. Cl.
CPC ....... *G01N 35/00871* (2013.01); *G06F 17/00* (2013.01); *G06F 19/28* (2013.01)

(56) References Cited

U.S. PATENT DOCUMENTS

| | | |
|---|---|---|
| 3,672,402 A | 6/1972 | Bloemer |
| 4,112,735 A | 9/1978 | Mcknight |
| 4,138,879 A | 2/1979 | Liebermann |
| 4,293,221 A | 10/1981 | Kay et al. |
| 4,371,786 A | 2/1983 | Kramer |
| 4,448,538 A | 5/1984 | Mantel |
| 4,559,454 A | 12/1985 | Kramer |
| 4,570,639 A | 2/1986 | Miodownik |
| 4,691,829 A | 9/1987 | Auer |
| 4,755,021 A | 7/1988 | Dyott |
| 4,774,189 A * | 9/1988 | Schwartz ........... G01N 15/1012 436/10 |
| 4,790,653 A | 12/1988 | North, Jr. |
| 4,818,103 A | 4/1989 | Thomas et al. |
| 4,824,641 A | 4/1989 | Williams |
| 4,826,660 A | 5/1989 | Smith et al. |
| 4,844,610 A | 7/1989 | North, Jr. |
| 4,933,813 A | 6/1990 | Berger |
| 5,028,127 A | 7/1991 | Spitzberg |
| 5,030,002 A | 7/1991 | North |
| 5,040,890 A | 8/1991 | North, Jr. |
| 5,043,706 A | 8/1991 | Oliver |
| 5,055,556 A | 10/1991 | Stryer et al. |
| 5,083,862 A | 1/1992 | Rusnak |
| 5,138,868 A | 8/1992 | Long |
| 5,139,609 A | 8/1992 | Fields et al. |
| 5,150,037 A | 9/1992 | Kouzuki |
| 5,150,313 A | 9/1992 | Van Den et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta et al. |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North, Jr. et al. |
| 5,403,552 A | 4/1995 | Pardikes |
| 5,466,946 A | 11/1995 | Kleinschmitt et al. |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,616,124 A | 4/1997 | Hague et al. |
| 5,684,480 A | 11/1997 | Jansson |
| 5,739,902 A | 4/1998 | Gjelsnes et al. |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,891,734 A * | 4/1999 | Gill ...................... B01F 5/0453 422/63 |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheimer |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,449,562 B1 * | 9/2002 | Chandler ................. C12Q 1/00 435/6.12 |
| 6,456,769 B1 | 9/2002 | Furusawa et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,568,271 B2 | 5/2003 | Shah et al. |
| 6,587,203 B2 | 7/2003 | Colon |
| 6,602,469 B1 | 8/2003 | Maus et al. |
| 6,636,623 B2 | 10/2003 | Nelson et al. |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 | 5/2005 | Sklar et al. |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,328,722 B2 | 2/2008 | Rich et al. |
| 7,362,432 B2 | 4/2008 | Roth |
| 7,403,125 B2 | 7/2008 | Rich |
| 7,471,393 B2 | 12/2008 | Trainer |
| 7,486,387 B2 | 2/2009 | Fritz |
| 7,520,300 B2 | 4/2009 | Rich et al. |
| 7,628,956 B2 | 12/2009 | Jindo |
| 7,738,099 B2 | 6/2010 | Morrell et al. |
| 7,739,060 B2 | 6/2010 | Goebel et al. |
| 7,776,268 B2 | 8/2010 | Rich |
| 7,780,916 B2 | 8/2010 | Bair et al. |

(56) References Cited

U.S. PATENT DOCUMENTS

| | | |
|---|---|---|
| 7,843,561 B2 | 11/2010 | Rich |
| 7,857,005 B2 | 12/2010 | Rich et al. |
| 7,981,661 B2 | 7/2011 | Rich |
| 7,996,188 B2 | 8/2011 | Olson et al. |
| 8,004,674 B2 | 8/2011 | Ball et al. |
| 8,017,402 B2 | 9/2011 | Rich |
| 8,031,340 B2 | 10/2011 | Rich et al. |
| 8,077,310 B2 | 12/2011 | Olson et al. |
| 2001/0014477 A1 | 8/2001 | Pelc et al. |
| 2001/0039053 A1 | 11/2001 | Liseo et al. |
| 2002/0028434 A1 | 3/2002 | Goix et al. |
| 2002/0049782 A1 | 4/2002 | Herzenberg et al. |
| 2002/0059959 A1 | 5/2002 | Qatu et al. |
| 2002/0080341 A1 | 6/2002 | Kosaka |
| 2002/0097392 A1 | 7/2002 | Minneman et al. |
| 2002/0098115 A1 | 7/2002 | Fawcett et al. |
| 2002/0123154 A1 | 9/2002 | Burshteyn et al. |
| 2002/0192113 A1 | 12/2002 | Uffenheimer et al. |
| 2003/0035168 A1 | 2/2003 | Qian et al. |
| 2003/0048539 A1 | 3/2003 | Oostman et al. |
| 2003/0054558 A1 | 3/2003 | Kurabayashi et al. |
| 2003/0062314 A1 | 4/2003 | Davidson et al. |
| 2003/0072549 A1 | 4/2003 | Facer et al. |
| 2003/0078703 A1 | 4/2003 | Potts et al. |
| 2003/0129090 A1 | 7/2003 | Farrell |
| 2003/0134330 A1 | 7/2003 | Ravkin et al. |
| 2003/0148379 A1 | 8/2003 | Roitman et al. |
| 2003/0151741 A1 | 8/2003 | Wolleschensky et al. |
| 2003/0175157 A1 | 9/2003 | Micklash et al. |
| 2003/0202175 A1 | 10/2003 | Van Den et al. |
| 2003/0211009 A1 | 11/2003 | Buchanan |
| 2003/0223061 A1 | 12/2003 | Sebok et al. |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0201845 A1 | 10/2004 | Quist et al. |
| 2004/0246476 A1 | 12/2004 | Bevis et al. |
| 2005/0044110 A1 | 2/2005 | Herzenberg et al. |
| 2005/0047292 A1 | 3/2005 | Park et al. |
| 2005/0057749 A1 | 3/2005 | Dietz et al. |
| 2005/0069454 A1 | 3/2005 | Bell |
| 2005/0073686 A1 | 4/2005 | Roth et al. |
| 2005/0078299 A1 | 4/2005 | Fritz et al. |
| 2005/0105091 A1 | 5/2005 | Lieberman et al. |
| 2005/0162648 A1 | 7/2005 | Auer et al. |
| 2005/0163663 A1 | 7/2005 | Martino et al. |
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |
| 2006/0023219 A1 | 2/2006 | Meyer et al. |
| 2006/0161057 A1 | 7/2006 | Weber et al. |
| 2006/0177937 A1 | 8/2006 | Kurabayashi et al. |
| 2006/0219873 A1 | 10/2006 | Martin et al. |
| 2006/0240411 A1 | 10/2006 | Mehrpouyan et al. |
| 2006/0281143 A1 | 12/2006 | Liu et al. |
| 2006/0286549 A1 | 12/2006 | Sohn et al. |
| 2007/0003434 A1 | 1/2007 | Padmanabhan et al. |
| 2007/0041013 A1 | 2/2007 | Fritz et al. |
| 2007/0059205 A1 | 3/2007 | Ganz et al. |
| 2007/0079653 A1 | 4/2007 | Zuleta et al. |
| 2007/0096039 A1 | 5/2007 | Kapoor et al. |
| 2007/0124089 A1 | 5/2007 | Jochum et al. |
| 2007/0127863 A1 | 6/2007 | Bair et al. |
| 2007/0134089 A1 | 6/2007 | Lee et al. |
| 2007/0144277 A1 | 6/2007 | Padmanabhan et al. |
| 2007/0188737 A1 | 8/2007 | Fritz |
| 2007/0212262 A1 | 9/2007 | Rich |
| 2007/0224684 A1 | 9/2007 | Olson et al. |
| 2007/0243106 A1 | 10/2007 | Rich |
| 2008/0055595 A1 | 3/2008 | Olson et al. |
| 2008/0064113 A1 | 3/2008 | Goix et al. |
| 2008/0092961 A1 | 4/2008 | Bair et al. |
| 2008/0152542 A1 | 6/2008 | Ball et al. |
| 2008/0215297 A1 | 9/2008 | Goebel et al. |
| 2008/0228444 A1 | 9/2008 | Olson et al. |
| 2008/0240539 A1 | 10/2008 | George et al. |
| 2008/0263468 A1 | 10/2008 | Cappione et al. |
| 2009/0104075 A1 | 4/2009 | Rich |
| 2009/0174881 A1 | 7/2009 | Rich |
| 2009/0201501 A1 | 8/2009 | Bair et al. |
| 2009/0202130 A1 | 8/2009 | George et al. |
| 2009/0216478 A1 | 8/2009 | Estevez-Labori |
| 2009/0260701 A1 | 10/2009 | Rich et al. |
| 2009/0276186 A1* | 11/2009 | Salinas ............ G01N 15/1425 702/188 |
| 2009/0293910 A1 | 12/2009 | Ball et al. |
| 2010/0012853 A1 | 1/2010 | Parks et al. |
| 2010/0032584 A1 | 2/2010 | Dayong et al. |
| 2010/0118298 A1 | 5/2010 | Bair et al. |
| 2010/0119298 A1 | 5/2010 | Huang |
| 2010/0120059 A1 | 5/2010 | Yan et al. |
| 2010/0271620 A1 | 10/2010 | Goebel et al. |
| 2010/0302536 A1 | 12/2010 | Ball et al. |
| 2010/0319469 A1 | 12/2010 | Rich |
| 2010/0319786 A1 | 12/2010 | Bair et al. |
| 2011/0008816 A1 | 1/2011 | Ball et al. |
| 2011/0058163 A1 | 3/2011 | Rich |
| 2011/0061471 A1 | 3/2011 | Rich et al. |
| 2011/0204259 A1 | 8/2011 | Rogers et al. |

FOREIGN PATENT DOCUMENTS

| | | |
|---|---|---|
| EP | 1391611 A | 2/2004 |
| EP | 1396736 A | 3/2004 |
| EP | 1521076 A | 4/2005 |
| JP | 356169978 | 12/1981 |
| JP | 04086546 H | 3/1992 |
| JP | 6194299 A | 7/1994 |
| JP | 06221988 H | 12/1994 |
| JP | 7260084 A | 10/1995 |
| JP | 08201267 H | 8/1996 |
| JP | 09288053 H | 11/1997 |
| JP | 10227737 A | 8/1998 |
| JP | 2001050887 A | 2/2001 |
| JP | 2001170062 A | 6/2001 |
| JP | 2003262201 A | 9/2003 |
| JP | 200477484 | 3/2004 |
| JP | 4065654 B2 | 3/2008 |
| JP | 2008197043 A | 8/2008 |
| WO | 9915905 A | 4/1999 |
| WO | 9956052 | 11/1999 |
| WO | 0194914 | 12/2001 |
| WO | 2004003504 A2 | 1/2004 |
| WO | 2005017499 A | 2/2005 |
| WO | 2005068971 A | 7/2005 |
| WO | 2005073694 A | 8/2005 |
| WO | 2005091893 A | 10/2005 |
| WO | 2006055722 A | 5/2006 |
| WO | 2007067577 A | 6/2007 |
| WO | 2007100723 A | 9/2007 |
| WO | 2007103969 A | 9/2007 |
| WO | 2007136749 A | 11/2007 |
| WO | 2008058217 A | 5/2008 |
| WO | 2010101623 A | 9/2010 |
| WO | 2011106402 A | 9/2011 |
| WO | 2011159708 A | 12/2011 |
| WO | 2012030740 A | 3/2012 |

OTHER PUBLICATIONS

Rogers et al., "The Benefits of Reducing Unnecessary Variability of Flow Cytometers," Accuri Cytometers [online], Dec. 2009 [retrieved on Apr. 12, 2011] Retrieved from the Internet: <URL:

(56) References Cited

OTHER PUBLICATIONS http://accuricytometers.com/files/Accuri_Reducing_Variability_Poster.pdf>.

Trotter, Compensation: An Instrumental Perspective, BD Biosciences [online], Sep. 10, 2003 [retrieved on Apr. 12, 2011], Retrieved from the Internet<URL: http://flowcytometry.uchc.edu/resources/pdfs/trotter_instrument_comp.pdf.

* cited by examiner

SYSTEM AND METHOD FOR CREATING A FLOW CYTOMETER NETWORK

CROSS-REFERENCE TO RELATED APPLICATIONS

This application claims the benefit of U.S. Provisional Application No. 61/354,577 filed 14 Jun. 2010, which is incorporated in its entirety by this reference.

TECHNICAL FIELD

This invention relates generally to the flow cytometer field, and more specifically to a new and useful system and method for creating a flow cytometer network in the flow cytometer field.

BACKGROUND

In recent years, flow cytometry has seen advances resulting in desktop-sized flow cytometers. These technological advances have also led to flow cytometers becoming more affordable. With this trend, more laboratories and clinical environments can afford to devote the effort and expense to operate one or multiple flow cytometers, enabling more experiments to be conducted and generating more flow cytometry data. Typically, only those using a particular flow cytometer or those in the same facility are able to use data generated by that flow cytometer. Furthermore, even if data from multiple flow cytometers is to be shared, there are problems with interoperability and comparability of data between flow cytometers. Collaboration and use of multiple flow cytometers is problematic in that the calibration of a single conventional flow cytometer is required prior to performing a particular experiment and involves numerous parameters tailored to that particular experiment. Thus, there is a need in the flow cytometer field to create a new and useful system and method for creating a flow cytometer network. This invention provides such a new and useful system and method.

DESCRIPTION OF THE PREFERRED EMBODIMENTS

Figure 1:
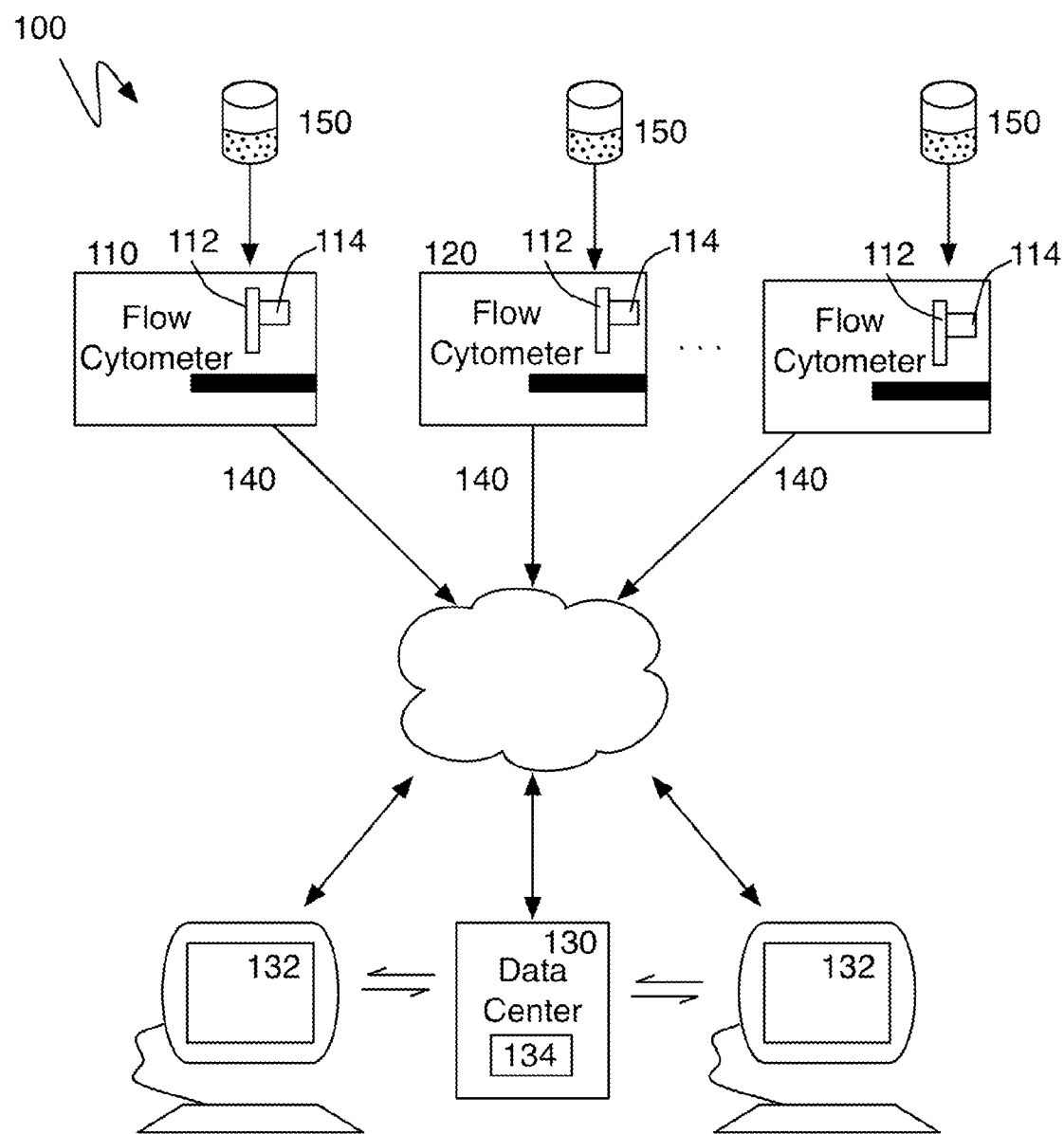
FIG. 1 is a schematic representation of a system for creating a flow cytometer network of a preferred embodiment.

The following description of preferred embodiments of the invention is not intended to limit the invention to these preferred embodiments, but rather to enable any person skilled in the art to make and use this invention.
System for Creating a Flow Cytometer Network As shown in FIG. 1, a system 100 of the preferred embodiment preferably includes: a flow cytometer 110 having an interrogation zone 112 through which a flow cytometer sample passes and a fixed gain detection system 114 configured to collect for the sample a sample data set of photonic inputs from the interrogation zone; a flow cytometer data center 130 that stores and manages sample-related data from the flow cytometer; and a network communication module 140 communicatively coupled to the flow cytometer and the flow cytometer data center 130, such that the network communication module 140 communicates sample-related data between the flow cytometer and the flow cytometer data center 130. The system preferably further includes at least a second flow cytometer substantially similar to the first flow cytometer and a second network communication module 140 communicatively coupled to the second flow cytometer and the flow cytometer data center 130. The system 100 primarily functions to create a data environment supplied with information from a plurality of flow cytometers. The environment may be located within a lab, a research center, or may be distributed across a worldwide data network. The system 100 frees researchers, clinicians, and other flow cytometer users from being restricted to relying on data only from flow cytometers within immediate reach (e.g., in a single laboratory room), and/or provides improved project collaboration between labs in different locations. As an exemplary application of the system, a plurality of flow cytometers may be spread throughout a company, such as throughout a single building or across different buildings and/or geographical locations. In another exemplary application, data from flow cytometers collected from across the country and/or world can be used by organizations like the Center for Disease Control and Prevention (CDC) for high level analysis of diseases and infections. In yet another exemplary application of the system, the system allows one to compile a cross-population comparison of data from a plurality of flow cytometers and perform a search for outliers among the compiled data, such as for identifying individual machines that have abnormal specifications and/or subject to possible experimental error. In addition, when the system includes flow cytometers with accurate volume count and/or flow rates, the system enables cross-instrument comparisons of concentrations. The system may additionally be applied to new processing and analysis techniques that leverage potentially large and accessible data.

The first flow cytometer 110 and the second flow cytometer 120 include an interrogation zone 112 through which a sample passes and provides photonic inputs, and a detection system 114 that collects for the sample a sample data set of the photonic inputs from the interrogation zone. The first and second flow cytometers are preferably substantially similar. For instance, the first and second flow cytometers preferably have comparable fixed gain detection systems that are each calibrated to a calibration solution 150 or fluid. In a preferred embodiment, calibration may be similar to that described in U.S. patent application No. 2010/0302536 entitled "Data collection system and method for a flow cytometer", which is incorporated in its entirety by this reference. The fixed gain detection system preferably enables data from different flow cytometers when communicatively coupled to the flow cytometer data center 130. There may be two, three, or any suitable number of flow cytometers used with the system. Any particular two flow cytometers in the plurality of flow cytometers may be the same or different models of flow cytometers. In a preferred embodiment, the first and second flow cytometers are preferably similar to that described in U.S. patent application No. 2006/0219873 entitled "Detection system for a flow cytometer", which is incorporated in its entirety by this reference. However, the flow cytometers may be any suitable flow cytometer, preferably with a fixed gain detection system.

Figure 2:
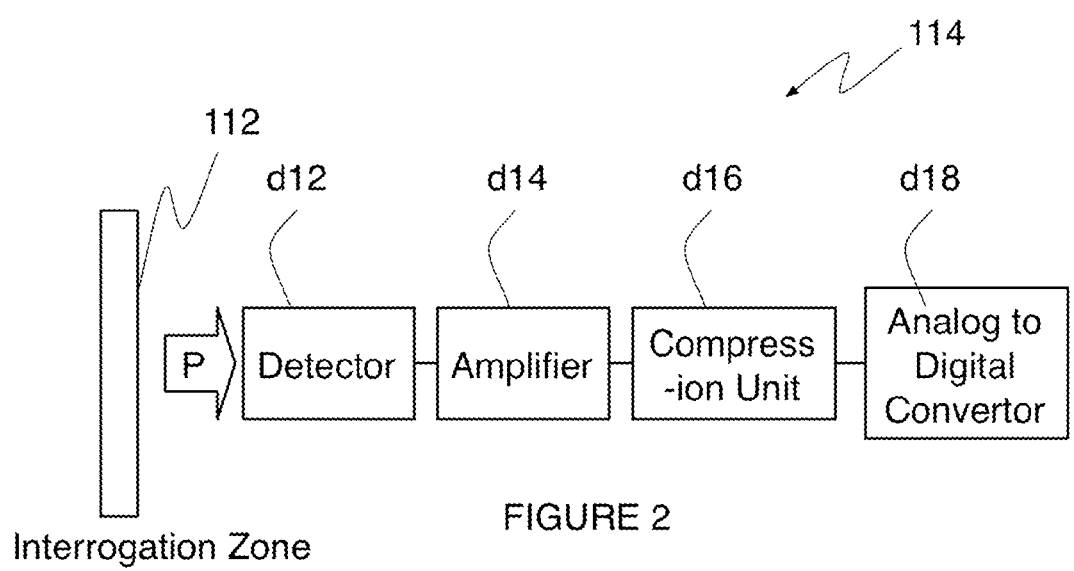
FIG. 2 is a detailed representation of the fixed detection system of a system for creating a flow cytometer network of a preferred embodiment.

As shown in FIG. 2, the detection system 114 of the preferred embodiment functions to collect photonic input data for a plurality of fluorescence channels. A fluorescence channel is a sample of data for a spectral range of light where fluorescence from a fluorochrome is most concentrated. The detection system preferably detects four fluorescence channels, but the detection system may between two to eight fluorescence channels, or any suitable number of fluorescence channels. The detection system 114 is preferably a fixed gain detection system that enables calibration of a flow cytometer that is universal or at least comparable between multiple flow cytometers with the fixed gain detection system. The fixed gain detection system further functions to allow simultaneous collection of both faint (e.g. small) objects and bright (e.g. large) objects by the flow cytometer, such that experiment-specific calibration for the objects of interest is not required. The first and second flow cytometers are able to output data that is comparable even when the experiment and sample differ greatly. Unlike conventional flow cytometers, the fixed gain detection system preferably does not require calibration or adjustments to the gain settings of the detection system (including human and/or computer or automatic calibration of the detection system) tailored each particular experiment type. In other words, adjustments and calibration of the gain settings of the detection system are preferably not required immediately prior to performing experiments with varying kinds of samples. In other words, the voltage and gain for the detection system are preferably fixed (e.g. during manufacture). In a preferred embodiment, the detection has a user interface similar to that described in U.S. patent application No. 2008/0228444 entitled "User interface for a flow cytometer system", which is incorporated in its entirety by this reference. However, alternatively the system may include a plurality of flow cytometers with different kinds of detection systems that are intentionally synchronized in any suitable manner to have substantially identical gain settings.

The detection system 114 preferably has a wide dynamic range, or ability to collect signals across a wide range of inputs. The wide dynamic range is preferably defined as a range of photonic input signals that provides a 1:100,000 ratio, and more preferably a 1:1,000,000 ratio (six decade range), between the faintest objects and the brightest objects. Additionally, the wide dynamic range preferably enables the flow cytometer to detect particles of the sample that are disparate in size, such as ranging from 1 micron up to 100 microns. For example, the wide dynamic range enables co-detection of mammalian cells (average diameter of 10-30 microns) and bacteria (average diameter of 0.5 microns), which have relative diameters that are disparate enough that they generally cannot be properly detected using a single gain setting on a typical flow cytometer. However, the detection system 114 with a wide dynamic range may simultaneously detect both the mammalian cells and bacteria cells. However, the detection system may alternatively allow for any suitable dynamic range such that the gain is substantially fixed. Once a fixed gain detection system has been calibrated (such as during manufacturing and/or for custom fluorochromes, preferably performed once by a user), the output of the detection system preferably represents an absolute photon count (or other suitable photometric unit). A data output is preferably photons/second, watts, or any similar absolute units. This photometric capability functions to allow absolute measurements from other detection systems in other flow cytometers to be directly compared to one another, without compensating for different calibration settings and/or gain settings for the individual flow cytometers. Examples of possible applications include FRET (fluorescence resonance energy transfer) based cytometric assays, absolute MESF (molecules of equivalent soluble fluorophore) measurements or similar metrics for the emission levels of cytometry calibration beads across production lots. For instance, MESF data may be calculated using the calibrated intensity of the excitation laser at the interrogation zone and the output of the fixed gain detection system. The wide dynamic range, along with the fixed gain characteristic, alleviates the need for individual tailored adjustments to the detectors or settings of the detection system.

The first and second flow cytometers are preferably calibrated to have substantially identical gain settings, such as during manufacturing, regular calibration checks, or any suitable time. For instance, both flow cytometers may be calibrated with a calibration solution 150, which functions as a standardized sample with set characteristics. The fixed detection system preferably distinguishes a set number of peaks within each fluorescence channel of the fixed detection system when the calibration solution sample passes through the interrogation zone. The calibration fluid 150 is preferably a pre-diluted fluid solution of calibration beads, such as Spherotech™ 6-peak beads, Spherotech™ 8-peak beads, or any suitable type of calibration beads. Calibration data generated from sampling the calibration solution may be used to validate data in the flow cytometer data center 130, and/or to interpret data accessed from the flow cytometer data center 130 so that data can be compared between flow cytometers with differing calibration data (e.g. for interpolation between data sets from different flow cytometers). Calibration of the flow cytometer may generate a calibration file that includes calibration data and/or any suitable calibration information (e.g. date, time, flow cytometer location) generated during the calibration.

As shown in FIG. 2, the detection system 114 preferably includes a detector d12, and may further include an amplifier d14 coupled to the detector, a compression unit d16 that is coupled to the amplifier d14, and/or an analog-to-digital converter (ADC) d18. The detector d12 functions to receive photonic inputs P from the interrogation zone 112. The detector preferably produces analog signals based on the photonic inputs P, and is preferably operable over a wide dynamic range as described above. The detector preferably has a luminous sensitivity of at least 80-120 microamps per lumen, but may alternatively have a luminous sensitivity of any suitable level. The detector is preferably operable to detect a light spectral range of approximately 400-700 nanometers, but may alternatively be operable over any suitable spectral range. The detector preferably includes one or more PIN photodiodes, which receive photonic inputs P from the interrogation zone and convert the impending electromagnetic radiation into an electrical signal. The PIN diodes are preferably adjusted during a manufacturing process of the detection system, to optimize their detection within a predetermined range. For example, the PIN diodes may be adjusted with a minimum detection above the optical and electrical "noise floor" of the detection system and are set with a maximum detection near the "operation ceiling" of the detection system. The adjustment preferably incorporates the use of calibration beads, but any other suitable method may be used. However, the detector may additionally and/or alternatively use any suitable detection device, such as specialized photomultipliers or other photodiodes.

The amplifier d14 is preferably coupled to the detector d12 such that the amplifier receives the electrical signal of the detector and amplifies the signal by a predetermined amount, depending upon the strength of the output and the breadth of the detector range. Although the amplifier preferably operates in the electrical domain (e.g. an avalanche photodiode that provides electrical amplification), the amplifier may alternatively operate in the optical domain (e.g. a laser that provides optical amplification). The amplifier may be integrated or partially integrated into the detector. The preferred amplifier has a signal-to-noise ratio ranging between approximately 100 dB and 120 dB.

The compression unit d16 is preferably coupled to the amplifier d14 and functions to reduce the dynamic range of the plurality of electrical signals from the amplifier and compress that data into an electrical signal with a smaller dynamic range, such as one that is appropriate for the ADC. In a preferred embodiment, the detection system incorporates signal compression to obtain better resolution for the input signals in the lower end of the signal range. The compression unit preferably uses a nonlinear compression algorithm, such as a logarithmic compression algorithm, but may use a linear, parametric, or any other suitable approach.

The analog-to-digital converter (ADC) d18 is preferably coupled directly or indirectly to the detector and configured to convert an analog signal to a digital signal that is readily usable by a digital circuit, process, or other computing device. The ADC preferably has a high bit resolution that is greater than or equal to 16 bits, and more preferably greater than or equal to 24 bits, which translates to roughly 16,700,000 levels of information, but the ADC may alternatively have any suitable bit resolution. The ADC preferably includes an SNR ratio of greater than approximately 100 dB, but may alternatively include a SNR of any suitable value.

In a first variation, the detection system 114 may include multiple detectors preferably operate on the same photonic input from the interrogation zone, but cover substantially different (overlapping or non-overlapping) subsets of the dynamic range of the photonic input. This allows one or more detectors to divide the responsibility of a single detector. In this variation, each detector preferably has a smaller dynamic range (e.g. on the order of 50-60 dB), set at different portions (overlapping or non-overlapping) of the dynamic range of the photonic input. Each detector preferably is coupled to a respective amplifier. The multiple amplifiers may have substantially identical gain and/or SNR values, or may have different gain and/or SNR values (e.g. a high-gain amplifier may be matched with one detector, and a low-gain amplifier may be matched with another detector).

In a second variation, the detection system 114 may include multiple amplifiers that operate on the output from the detector (or each of multiple detectors), but amplify the analog signal from the detector at different gain levels. This allows more than one amplifier to divide the responsibility of a single amplifier. In this variation, the amplifiers may be set at distinct gain levels (e.g., one amplifier is set at a higher gain level, and another amplifier is set at a lower gain level). Alternatively, the multiple amplifiers may be set at similar gain levels.

The flow cytometer data center 130 functions to store and manage data from one, or preferably multiple, flow cytometers. The flow cytometer data center 130 is preferably network-accessible and includes a server and a database that stores sample-related data from the flow cytometers. The data center may include a web application interface 132 or any suitable portable, accessible by researchers, clinicians, and other users. The data center preferably implements any suitable security and permission restrictions to restrict access or filter information, such as to comply with patient privacy regulations. In one variation, the flow cytometer data center includes an application programming interface (API), which can be used to target and retrieve particular types of data during the analysis, such as data sets regarding a particular type of sample or experiment, data sets collected by related groups of flow cytometers, data sets collected across a particular geographical region, or any suitable kind of data. Other parties may use the API to implement additional or alternative applications for interacting with the flow cytometer data center. The API is preferably a web API such as a Representational State Transfer (REST) style API or a Simple Object Access Protocol (SOAP) style API, but may alternatively be any suitable type of API.

The flow cytometer data center 130 preferably stores one or more types of sample-related data. In one variation, the data center 130 stores data analysis information, or analysis data from flow cytometers after the flow cytometers have analyzed sample data after an experiment. The data analysis information may be any suitable data or file generated by analysis/processing for the experiment, such as absolute counts, tables, or plots. Storing the data analysis information preferably enables the analysis and post-processing of raw sample data set to be shared. For example, in this variation, researchers or clinicians can view and incorporate prior analyses performed by other user. The experimental analysis, coupled with the raw data, may additionally be used with a neural network algorithm or other pattern detection algorithm to detect patterns that exist, for instance, in raw data and/or analysis of the raw data of a particular characteristic. The analysis patterns can then be automatically applied to future raw data having the same or similar particular characteristic.

In another variation, as shown in FIG. 1, the flow cytometer data center 130 includes an analyzer 134 that evaluates sample-related data from one or more flow cytometers. For instance, the analyzer 134 may include an independent processor that analyzes a sample data set remotely from the flow cytometer that performed a particular experiment and gathered the sample data. As another example involving cloud computing, the analyzer may be coupled to a plurality of processors that collectively analyze a sample data set remotely from the flow cytometer that gathered the sample data set.

In another variation, the data center 130 stores the sample experimental data set, including raw flow cytometry data from an experiment. In other variations, the flow cytometer data stores a calibration file, sample information, or laboratory information. The calibration file includes information generated during calibration of the device, such as or day, time, activities performed, calibration readouts, identification information pertaining to the service technician (or in an alternative embodiment, the user) who performed the calibration, and information for identifying the relevant flow cytometer. The sample information may include any information for identifying the relevant sample, such as types of substance (e.g. blood), type of preparation such as an added lysis, descriptions of sample origin such as patient parameters such as age or sex, or any suitable information about the test sample. The laboratory information preferably include any meta data about the lab or clinic, such as operator of the flow cytometer, laboratory name, research project name, geographical location, name of company, time of experiment, references to related batches of experiments, or any suitable parameter or other information. For example, geographical location information stored by the flow cytometer data center 130 can be used to perform geographical analysis of experimental results, such as tracking the spread of diseases. The laboratory information may additionally and/or alternatively be used to create a network of experimental data similar to a social network, with experimental references between data, analysis, and/or research. However, in other variations the flow cytometer data center 130 may store any suitable kind of information and the data may be used in any suitable manner.

The network communication module 140 functions to communicate sample-related data between the flow cytometer and the flow cytometer data center 130, including uploading to and downloading from the data center. The network communication module may communicate any of the types of data stored by the flow cytometer data center, including raw sample data, sample analysis data, calibration files, or laboratory information. The network communication module 140 preferably includes an Ethernet port or other network port, a Wi-Fi modem, or any suitable port to connect to a network. The network communication module preferably communicates through the internet, but may additionally and/or alternatively communicate through an intranet system such as for a system implemented for internal operations. The network communication module preferably communicates with any suitable network protocol, such as a hypertext transfer protocol (HTTP). In one variation, the network communication module 140 automatically uploads and/or downloads sample-related data to the flow cytometer data center, such as after every experimental sample run, after a particular number of experimental sample runs, after every experimental sample run of a particular type, at particular time intervals (e.g. every day or every hour) or any suitable event and/or period of time. In another variation, the flow cytometer includes a user interface, coupled to the network communication module, that enables the user to selectively upload and/or download sample-related data at desired times. In some variations, the system may enable both automatic and user-selected uploading to and/or downloading from the flow cytometer data center. The flow cytometer data center may be communicatively coupled to any number of additional data centers or storage sites, such as for data backup purposes.

Method for Creating a Flow Cytometer Network

Figure 3:
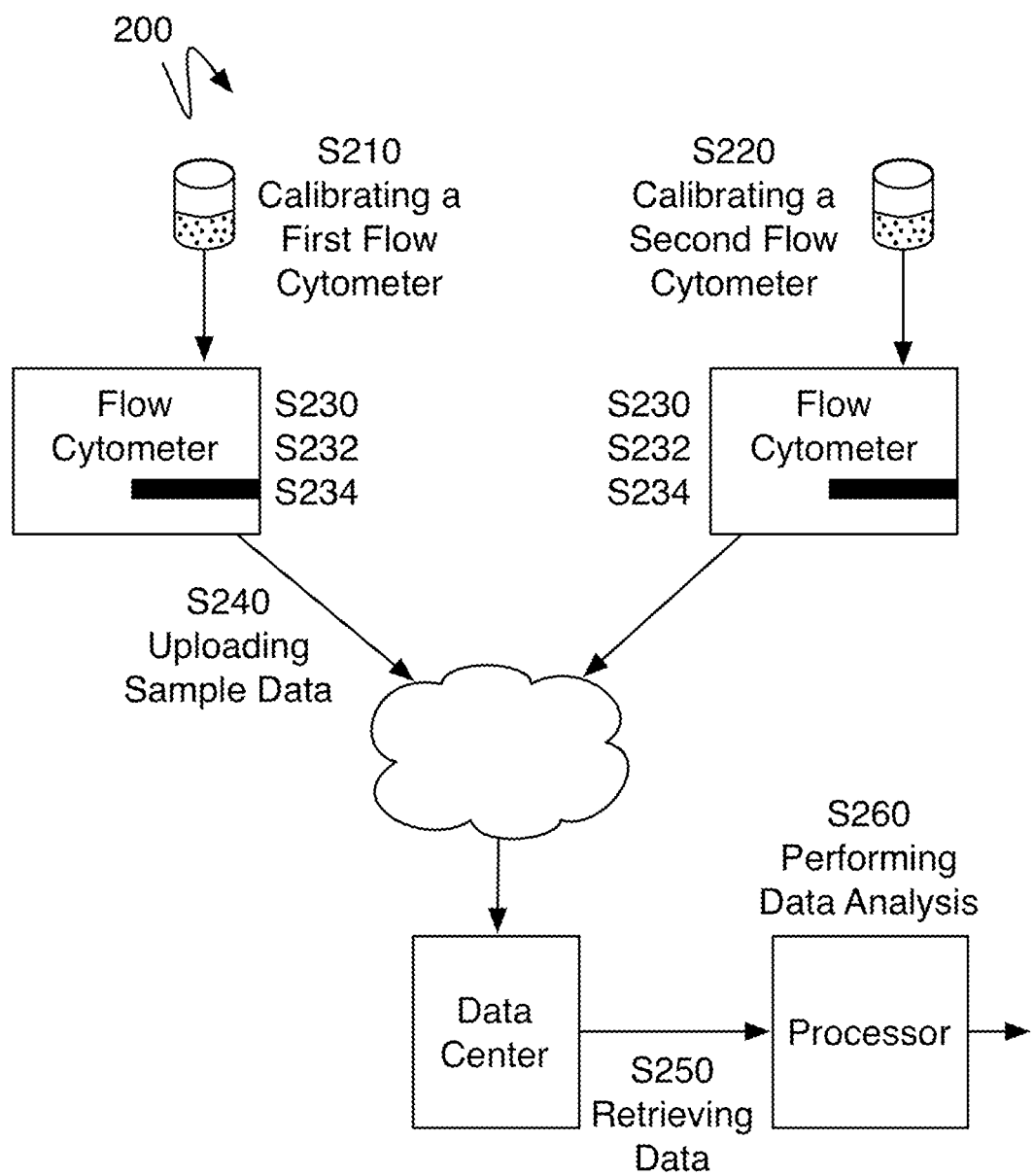
FIG. 3 is a schematic representation of a method for creating a flow cytometer network of a preferred embodiment.

As shown in FIG. 3, a method 200 for creating a flow cytometer network of a preferred embodiment includes calibrating a first flow cytometer S210 with a calibration solution, calibrating a second flow cytometer S220 with the calibration solution, collecting a sample data set for a sample S230 with a fixed gain detection system, uploading sample-related data S240 from each of the first and second flow cytometers to a flow cytometer data center, retrieving flow cytometry data S250 from the flow cytometer data center, and performing data analysis S260 on flow cytometer data from the flow cytometer data center. The method 200 may additionally and/or alternatively include collecting photonic inputs from an interrogation zone across a wide dynamic range S232. The method functions to create interoperable data from a plurality of flow cytometers that enables widescale data set analysis. The method can be used for large data set analysis, for analysis on data collected from various locations, and/or for any suitable application.

Calibrating a first flow cytometer S210 and calibrating a second flow cytometer S220 function to calibrate a plurality of flow cytometers to a standard reference sample. The first and second flow cytometers each preferably includes a fixed gain detection system that alleviates numerous calibration steps, and functions to allow calibration to a standard calibration fluid, instead of calibrating and adjusting gain to settings tailored for a particular sample and experiment.

Collecting a sample data set S230 for a sample with a fixed gain detection system preferably includes collecting photonic inputs from an interrogation zone of the flow cytometer for a plurality of fluorescence channels, generating an analog signal based on the photonic inputs, and converting the analog signal to a digital signal. Collecting photonic inputs preferably includes collecting photonic inputs from an interrogation zone across a wide dynamic range S232. Collecting a sample data set S230 is preferably performed by a detection system substantially similar to that described above. A fixed gain detection system preferably outputs absolute photometric units (such as an absolute photon count), and collects a sample data set without accepting a gain amplification level selection from the user. An additional step may include calculating an absolute MESF using the intensity of laser excitation at the interrogation zone and the output of the detection system. Generating an analog signal is preferably performed by an analog-to-digital converter substantially similar to the analog-to-digital converter described above. The step of collecting a sample data may additionally and/or alternatively be performed by any suitable system or in any suitable manner.

Step S230 may additionally include performing analysis on the collected data set S234, which functions to provide another layer of accessibility to the data once the data is uploaded to a data center. The analysis and/or processing preferably converts the raw data into a format used by experimenters (e.g. plots). There may be any number of process steps performed on the data. Some exemplary analysis steps performed on data may include the generate of relevant plots, such as enlarged plots of particular fluorescence channels and set gating parameters. The processing and analysis are preferably stored in an application data format created by an application performing the processing. The processing and analysis may alternatively be described in a standardized format such as a markup language. The analysis data is preferably additionally uploaded to the data center in step S240.

Uploading sample-related data S240 functions to send data from the flow cytometers so that the data is accessible through the network from the data center. Data collected from a plurality of flow cytometers is preferably uploaded to the data center, and may include raw sample data, data analysis information, a calibration file, laboratory information, sample information, and/or any suitable data. The uploading preferably occurs in a background processing step, but may additionally and/or alternatively be triggered by a user-selectable action. Sample-related data may be uploaded as changes to the data are made. For example, raw experimental data may be uploaded following collection, and data analysis information may be uploaded after a researcher or clinician performs analysis on the raw experimental data.

Retrieving flow cytometer data from the flow cytometer data center S250 functions to download data from the data center through the flow cytometer network. Data can be fetched and queried through the data center (e.g. through an API). Data querying can be used to target and retrieve particular types of data during the analysis, such as data sets regarding a particular type of sample or experiment, data sets collected by related groups of flow cytometers, data sets collected across a particular geographical region, or any suitable kind of data.

Performing data analysis on flow cytometry data from the flow cytometer data center S260 functions to use data set from one or more flow cytometers for analysis. The substantially similar fixed gain detection systems of the flow cytometers preferably enable the data from the flow cytometers to be easily combined into a single data set prior to performing data analysis. This data combination preferably functions to improve signal-to-noise of rare events and/or difficult to resolve experiments. In one application of analysis, a search is conducted for outliers within a cross-population comparison of a plurality of flow cytometers. Individual flow cytometers may be identified by this comparison as being out-of-spec, being subject to possible experimental error, and/or having any suitable abnormal condition or characteristics. In another application, when the flow cytometers include accurate volume count and/or flow rates, the fixed gain detection systems enable an accurate comparison of concentrations to be performed across experiments from multiple flow cytometers. The data center may alternatively be used to identify an experimental sample that a researcher or clinician does not have access to. The data analysis may use geographic location, patient age, sample type, temporal variables, or any suitable parameter as an additional metric in the analysis. For example, data from across the country may be analyzed to track and/or predict spread of a disease, especially as results of more tests from additional flow cytometers are added to the network. Immunization allocation, research funding, and disease preventative actions can all be more readily controlled using the flow cytometer network and data center. In another variation, large data sets may be used to algorithmically learn analysis processes. Through analysis of large datasets, analysis processes may be linked with raw data patterns using a neural network or any suitable learning algorithm. When raw data is identified to match a particular pattern, analysis on the data may be automatically performed and/or initiated by the user. Furthermore, information on this data analysis on uploaded data may also be uploaded to the data center.

As a person skilled in the art will recognize from the previous detailed description and from the figures and claims, modifications and changes can be made to the preferred embodiments of the invention without departing from the scope of this invention defined in the following claims.

We claim:

1. A system for creating a flow cytometer network, comprising:
   a first and second flow cytometers, each flow cytometer respectively including:
      an interrogation zone through which a flow cytometer sample passes; and
      a fixed gain detection system configured to use a fixed gain setting for collecting for the sample a sample data set of photonic inputs from the interrogation zone;
   a flow cytometer data center that stores and manages sample-related data from the first and second flow cytometers, the flow cytometer data center comprising an analysis module configured to perform data analysis by directly comparing the sample data sets from the first and the second flow cytometers without compensating for differences between the fixed gain settings of the first and the second flow cytometers, and without compensating for differences in calibration settings of the first and the second flow cytometers; and
   a network communication module communicatively coupled to at least one of the first and the second flow cytometers and the flow cytometer data center, wherein the network communication module communicates sample-related data between the at least one of the first and the second flow cytometers and the flow cytometer data center.

2. The system of claim 1, wherein the fixed gain detection system of the first flow cytometer is configured to collect a sample data set that includes a wide dynamic range of photonic inputs.

3. The system of claim 2, wherein the fixed gain detection system of the first flow cytometer is configured to collect a sample data set that includes at least a 1:100,000 ratio between the faintest objects and the brightest objects.

4. The system of claim 3, wherein the fixed gain detection system of the first flow cytometer is configured to collect a sample data set that includes at least a 1:1,000,000 ratio between the faintest objects and the brightest objects.

5. The system of claim 1, wherein the network communication module automatically uploads sample-related data to the flow cytometer data center.

6. The system of claim 1, wherein the first and the second flow cytometers each includes a user interface through which a user may selectively upload sample-related data to the flow cytometer data center.

7. The system of claim 6, wherein the user interface enables the user to download uploaded sample-related data from the flow cytometer data center.

8. The system of claim 1, wherein the flow cytometer data center includes a server and a database, and is network-accessible.

9. The system of claim 8, wherein the flow cytometer data center includes a web application interface.

10. The system of claim 8, wherein the flow cytometer data center stores data analysis information.

11. The system of claim 10, wherein the flow cytometer data center further stores at least one of: the sample data set, a calibration file, and sample information.

12. The system of claim 8, wherein the flow cytometer data center is communicatively coupled to a plurality of flow cytometers.

13. The system of claim 7, wherein the flow cytometer data center includes an application programming interface (API).

14. The system of claim 1, wherein the first and second flow cytometers are calibrated with substantially identical calibration solutions.

15. The system of claim 1, wherein the first and second flow cytometers have substantially identical gain settings.

16. A method for creating a flow cytometer network, comprising:
   calibrating a first flow cytometer with a calibration solution;
   calibrating a second flow cytometer with the calibration solution;
   collecting, at the first flow cytometer a first sample data set for a first sample using a first fixed gain detection system with a first fixed gain setting;
   collecting, at the second flow cytometer a second sample data set for a second sample using a second fixed gain detection system with a second fixed gain setting;
   uploading the first and the second sample data sets to a flow cytometer data center;
   retrieving flow cytometry data from the flow cytometer data center; and
   performing, at the flow cytometer data center, data analysis by directly comparing the first and the second sample data sets without compensating for differences between the first fixed gain setting and the second fixed gain setting, and without compensating for differences in calibration settings of the first and the second flow cytometers.

17. The method of claim 16, wherein collecting a sample data set includes collecting sample data without accepting a gain amplification level selection from a user.

18. The method of claim 16, wherein collecting a sample data set with a fixed gain detection system includes collecting photonic inputs from an interrogation zone across a wide dynamic range that includes a 1:100,000 ratio between the faintest objects and the brightest objects.

19. The method of claim 16, wherein uploading the first and the second sample data sets includes uploading data analysis information.

20. The method of claim 16, wherein uploading the first and the second sample data sets includes uploading to the flow cytometer data center at least one of: a calibration file, the sample data set, sample information, and laboratory information.

21. The method of claim 16, wherein performing data analysis on data includes analyzing data collected from two or more flow cytometers.

22. The method of claim 16, further comprising uploading the data analysis to the flow cytometer data center.

23. A method for creating a flow cytometer network, comprising:
    calibrating a first flow cytometer with a calibration solution;
    calibrating a second flow cytometer with the calibration solution;
    collecting, at the first flow cytometer a first sample data set for a first sample using a first fixed gain detection system with a first fixed gain setting, wherein collecting the first sample data set includes collecting photonic inputs from an interrogation zone of the first flow cytometer across a wide dynamic range that includes at least a 1:100,000 ratio between the faintest objects and the brightest objects;
    collecting, at the second flow cytometer a second sample data set for a second sample using a second fixed gain detection system with a second fixed gain setting, wherein collecting the second sample data set includes collecting photonic inputs from an interrogation zone of the second flow cytometer across a wide dynamic range;
    uploading the first and the second sample data sets to a flow cytometer data center;
    retrieving flow cytometry data from the flow cytometer data center; and
    performing, at the flow cytometer data center, data analysis by directly comparing the first and the second sample data sets without compensating for differences between the first fixed gain setting and the second fixed gain setting.

24. The method of claim 23, wherein collecting sample data includes collecting sample data with a fixed gain detection system, without accepting a gain amplification level selection from a user.

25. A method for creating a flow cytometer network, comprising:
    calibrating a first flow cytometer with a calibration solution;
    calibrating a second flow cytometer with the calibration solution;
    collecting, at the first flow cytometer a first sample data set for a first sample using a first fixed gain detection system with a first fixed gain setting, wherein collecting the first sample data set includes collecting photonic inputs from an interrogation zone across a wide dynamic range that includes a 1:100,000 ratio between the faintest objects and the brightest objects;
    collecting, at the second flow cytometer a second sample data set for a second sample using a second fixed gain detection system with a second fixed gain setting;
    uploading the first and the second sample data sets to a flow cytometer data center;
    retrieving flow cytometry data from the flow cytometer data center; and
    performing, at the flow cytometer data center, data analysis by directly comparing the first and the second sample data sets without compensating for differences between the first fixed gain setting and the second fixed gain setting, and without compensating for differences in calibration settings of the first and the second flow cytometers.

* * * * *